United States Patent [19]
Baasner et al.

[11] Patent Number: 5,338,860
[45] Date of Patent: Aug. 16, 1994

[54] 4-(SUBSTITUTED)AMINO-3-ARYLPYR-ROLINONE DERIVATIVES

[75] Inventors: Bernd Baasner, Bergisch Gladbach; Reiner Fischer, Monheim; Arno Widdig, Odenthal-Blecher; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 985,377

[22] Filed: Dec. 4, 1992

[30] Foreign Application Priority Data

Dec. 16, 1991 [DE] Fed. Rep. of Germany ....... 4141399

[51] Int. Cl.$^5$ ............... C07D 207/263; A01N 43/36
[52] U.S. Cl. ................................................. 548/550
[58] Field of Search ........................ 548/550; 504/302

[56] References Cited

U.S. PATENT DOCUMENTS 4,643,762  2/1987  Ward ............................. 548/541
5,191,089  3/1993  Baasner et al. ................. 548/550

FOREIGN PATENT DOCUMENTS 0262399  4/1988  European Pat. Off. .
0377893  7/1990  European Pat. Off. .
0415185  3/1991  European Pat. Off. .

*Primary Examiner*—David B. Springer
*Attorney, Agent, or Firm*—Sprung Horn Kramer & Woods

[57] ABSTRACT

The invention relates to new 4-(substituted)amino-3-arylpyrrolinone derivatives of the general formula (I)

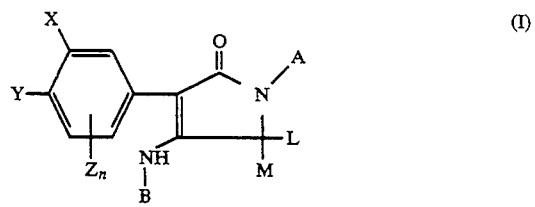

in which X, Y, Z, n, B, M, L and A are as defined in the description, to a process and new intermediates for their preparation, and to their use as herbicides.

8 Claims, No Drawings

4-(SUBSTITUTED)AMINO-3-ARYLPYRROLI-NONE DERIVATIVES

The invention relates to new 4-(substituted)amino-3-arylpyrrolinone derivatives, to processes and new intermediates for their preparation, and to their use as herbicides.

3-Acyl-pyrrolidine-2,4-diones have previously been described as having pharmaceutical properties (S. Suzuki et. al., Chem. Pharm. Bull. 15 1120 (1967)). N-Phenyl-pyrrolidine-2,4-diones were furthermore synthesised by R. Schmierer and H. Mildenberger, Liebigs Ann. Chem. 1985 1095. A biological activity of these compounds was not described.

EP-A 0,262,399 discloses compounds which have a similar structure (3-aryl-pyrrolidine-2,4-diones), but they are not known as having a herbicidal activity.

EP-A-0,415,185 discloses 4-alkoxy or 4-substituted amino-3-arylpyrrolinone derivatives and their use as herbicides.

EP-A 377,893 furthermore describes 3-arylpyrrolidine-2,4-dione derivatives which have an insecticidal, acaricidal and herbicidal action and which may have a hydroxyl in the 4-position of the pyrrolinone. Compounds listed in the abovementioned application EP-A-415,185 by name are excluded from the extent of protection of the present application by disclaimer.

There were now found new 4-(substituted)amino-3-arylpyrrolinone derivatives of the general formula (I)

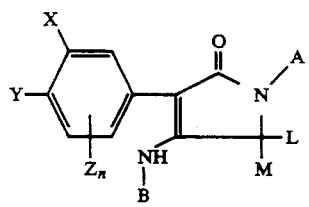

(I)

in which

X and Y independently of one another represent hydrogen, halogen, alkyl, alkoxy, alkylthio, halogenoalkoxy, halogenoalkyl, or in each case represent an unsubstituted or substituted radical from the series comprising aryl, aryloxy or arylthio, Z represents halogen, alkyl or alkoxy, n represents a number 0, 1, 2 or 3, A represents a radical from the series comprising alkyl, alkenyl, alkinyl, alkoxyalkyl, halogenoalkyl, polyalkoxyalkyl or alkylthioalkyl, each of which is unsubstituted or each of which is substituted by halogen, or represents cycloalkyl which is optionally interrupted by hetero atoms, or represents arylalkyl which is unsubstituted or substituted by halogen, alkyl, halogenoalkyl, alkoxy and/or nitro, or aryl which is unsubstituted or substituted by suitable substituents being halogen, alkyl, alkoxy, halogenoalkyl, halogenoalkoxy, or phenoxy or phenylthio, each of which is unsubstituted or substituted by halogen, alkyl, alkoxy, halogenoalkyl and/or halogenoalkoxy, B represents hydrogen, the group

or the group

,

L represents hydrogen, or represents an optionally halogen-substituted radical from the series comprising alkyl, alkenyl, alkinyl, polyalkoxyalkyl, alkoxyalkyl, alkylthioalkyl, cycloalkyl which is optionally interrupted by hetero atoms, or represents a radical from the series comprising aryl, arylalkyl or hetaryl, each of which is optionally substituted by halogen, alkyl, halogenoalkyl, alkoxy or nitro, M represents hydrogen, alkyl or alkoxyalkyl, or A and L or L and M together with the atoms to which they are bonded form a cycle and R represents an optionally halogen-substituted radical from the series comprising alkyl, alkenyl, alkinyl, alkoxyalkyl, polyalkoxyalkyl, alkylthioalkyl, cycloalkyl which is optionally interrupted by hetero atoms, or represents an aryl which is optionally substituted by halogen, alkyl, halogenoalkyl, alkoxy or nitro, and the enantiomeric forms of compounds of the formula (I) with the exception of the compounds 4-amino-1-isopropyl-3-(3-trifluoromethylphenyl)-3-pyrrolin-2-one and 4-amino-1-cyclopropyl-3-(3-trifluoromethylphenyl)-3-pyrrolin-2-one (EP 0,415,185).

Other sub-groups which may be defined are the following: (Ia): compounds of the formula (I) in which B=hydrogen (Ib): compounds of the formula (I) in which B=—COR (Ic): compounds of the formula (I) in which B=—COOR.

The aliphatic hydrocarbon chains such as, for example, alkyl, halogenoalkyl, arylalkyl or phenoxyalkyl, are in each case straight-chain or branched.

In the case of substituted systems such as, for example, substituted alkyl, alkenyl, cycloalkyl or aryl, these may in each case be monosubstituted or polysubstituted by identical or different substituents. Aromatic systems are preferably monosubstituted to pentasubstituted, in particular monosubstituted to trisubstituted, and cyclic systems are preferably monosubstituted to octasubstituted, in particular monsubstituted to pentasubstituted.

Furthermore, it has been found that the compounds of the formula (Ia)

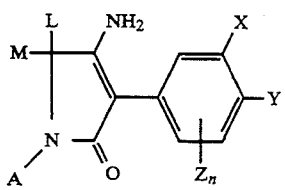

(Ia)

in which aα) B represents hydrogen and in which the radicals A, L, M, X, Y and $Z_n$ have the abovementioned meanings, are obtained when 4-hydroxypyrrolinones of the formula (II)

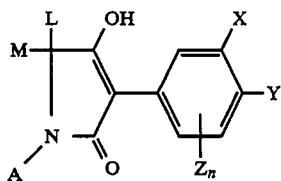

in which A, L, M, X, Y, Z and n have the abovementioned meanings, are reacted with ammonia or ammonia salts, if appropriate in the presence of a diluent, if appropriate in the presence of a catalyst and if appropriate in the presence of a dehydrating agent, or in that aβ) compounds of the formula (III)

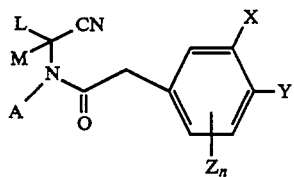

in which A, L, M, X, Y, Z and n have the abovementioned meanings, are subjected to intramolecular cyclisation in the presence of a diluent and in the presence of a base.

Furthermore, it has been found that compounds of the formula (Ib)

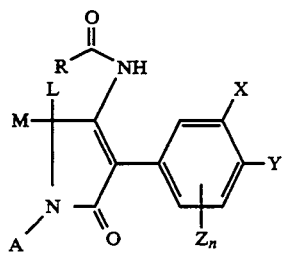

in which A, L, M, R, X, Y, Z and n have the abovementioned meanings, are obtained when compounds of the formula (Ia)

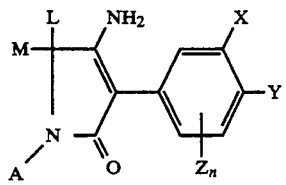

in which A, L, M, X, Y, Z and n have the abovementioned meanings, bα) are reacted with acid halides of the general formula (IV)

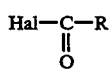

(IV)

in which
R has the abovementioned meaning and
Hal represents halogen, in particular chlorine and bromine, if appropriate in the presence of a diluent and if appropriate in the presence of an acid-binding agent, or bβ) are reacted with carboxylic anhydrides of the general formula (V)

R—CO—O—CO—R (V)

in which
R has the abovementioned meaning, if appropriate in the presence of a diluent and if appropriate in the presence of an acid-binding agent.

(c) Furthermore, it has been found that compounds of the formula (Ic)

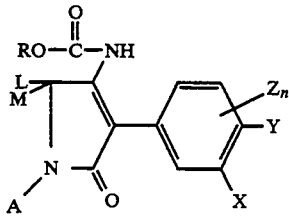

in which A, L, M, X, Y, Z, R and n have the abovementioned meanings, are obtained when compounds of the formula (Ia)

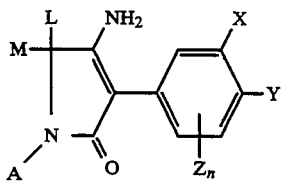

in which A, L, M, X, Y, Z and n have the above-mentioned meanings, are reacted with chloroformate of the general formula (VI)

R—O—CO—Cl (VI)

in which
R has the abovementioned meaning, if appropriate in the presence of a diluent and if appropriate in the presence of an acid-binding agent.

Finally, it has been found that the new 4-(substituted)-amino-3-arylpyrrolinones of the general formula (I) have herbicidal properties.

Surprisingly, the 4-(substituted)-amino-3-arylpyrrolinones of the general formula (I) according to the invention show an outstanding herbicidal activity combined with an excellent tolerance by important crop plants.

Preferred compounds of the formula (I) are those in which

X and Y independently of one another are hydrogen, fluorine, chlorine, bromine, iodine, $C_1$–$C_6$-alkyl, $C_1$–$C_6$-alkoxy, $C_1$–$C_6$-alkylthio, $C_1$–$C_6$-halogenoalkoxy, halogeno-$C_1$–$C_4$-alkyl, or a radical from the series comprising phenyl, phenoxy or phenylthio, each of which is unsubstituted or monosubstituted to penta-substituted by identical or different substituents, the following being selected as phenyl substituents: fluorine, chlorine, bromine, iodine, $C_1$-$C_4$-alkyl, $C_1$-$C_4$-alkoxy and halogeno-$C_1$-$C_4$-alkyl, Z represents fluorine, chlorine, bromine, iodine, $C_1$-$C_6$-alkyl or $C_1$-$C_6$-alkoxy, n represents a number 0, 1, 2 or 3, A represents a radical from the series comprising $C_1$-$C_{12}$-alkyl, $C_3$-$C_8$-alkenyl, $C_3$-$C_8$-alkinyl, halogeno-$C_1$-$C_8$-alkyl, $C_1$-$C_{10}$-alkoxy-$C_2$-$C_8$-alkyl, $C_1$-$C_8$-polyalkoxy-$C_1$-$C_8$-alkyl, $C_1$-$C_{10}$-alkylthio-$C_1$-$C_8$-alkyl, each of which is unsubstituted or each of which is substituted by halogen, or represents cycloalkyl which has 3 to 8 ring atoms and which can be interrupted by oxygen, nitrogen and/or sulphur, or A represents a radical from the series comprising phenyl-$C_1$- $C_6$-alkyl, phenyl or naphthyl, each of which is unsubstituted or monosubstituted to pentasubstituted in the phenyl moiety by identical or different substituents, selected substituents in each case being: fluorine, chlorine, bromine, iodine, $C_1$-$C_6$-alkyl, $C_1$-$C_6$-alkoxy, halogeno-$C_1$-$C_6$-alkyl, halogeno-$C_1$-$C_6$-alkoxy, or phenoxy or phenylthio, each of which is unsubstituted or monosubstituted to pentasubstituted by identical or different substituents from the series comprising fluorine, chlorine, bromine, iodine, $C_1$-$C_4$-alkyl, $C_1$-$C_4$-alkoxy, halogeno-$C_1$-$C_4$-alkyl and halogeno-$C_1$-$C_4$-alkoxy, B represents hydrogen, the group

or the group

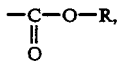

L represents hydrogen, or represents an optionally halogen-substituted straight-chain or branched radical from the series comprising $C_1$-$C_{12}$-alkyl, $C_3$-$C_8$-alkenyl, $C_3$-$C_8$-alkinyl, $C_1$-$C_{10}$-alkoxy-$C_2$-$C_8$alkyl, $C_1$-$C_8$-polyalkoxy-$C_2$-$C_8$-alkyl, $C_1$-$C_{10}$alkylthio-$C_2$-$C_8$-alkyl, cycloalkyl which has 3–8 ring atoms and which can be interrupted by oxygen and/or sulphur, or represents a radical from the series comprising aryl, hetaryl or aryl-$C_1$-$C_6$-alkyl, each of which is optionally substituted by halogen, $C_1$-$C_6$-alkyl-$C_1$-$C_6$-halogenoalkyl, $C_1$-$C_6$-alkoxy or nitro, M represents hydrogen or a straight-chain or branched radical from the series comprising $C_1$-$C_{12}$-alkyl, $C_1$-$C_8$-alkoxyalkyl, or in which A and L or L and M together with the atoms to which they are bonded form a 3 to 8-membered ring which can be saturated or unsaturated and substituted and/or interrupted by oxygen/sulphur, R represents an optionally halogen-substituted straight-chain or branched radical from the series comprising $C_1$-$C_{12}$-alkyl, $C_3$-$C_8$-alkenyl, $C_3$-$C_8$-alkinyl, $C_1$-$C_{10}$-alkoxy-$C_2$-$C_8$-alkyl, $C_1$-$C_8$-polyalkoxy-$C_2$-$C_8$-alkyl, $C_1$-$C_{10}$-alkylthio-$C_2$-$C_8$-alkyl, cycloalkyl which has 3–8 ring atoms and which can be interrupted by oxygen and/or sulphur, or represents aryl which is optionally substituted by halogen, $C_1$-$C_6$-alkyl-$C_1$-$C_6$-halogenoalkyl, $C_1$-$C_6$-alkoxy or nitro, and the enantiomeric forms of compounds of the formula (I) with the exception of the compounds: 4-amino-1-cyclopropyl-3-(3-trifluoromethylphenyl)-3-pyrrolin-2-one and 4-amino-1-isopropyl-3-(3-trifluoromethylphenyl)-3-pyrrolin-2-one.

A particularly preferred group of compounds of the formula (I) are those in which X represents hydrogen, fluorine, chlorine, bromine, methyl, ethyl, n- or iso-propyl, methoxy, ethoxy, n- or i-propoxy, halogenomethyl having 1, 2 or 3 fluorine and/or chlorine atoms, halogenoethyl having 1 to 5, in particular 1 to 3, fluorine and/or chlorine atoms, $C_1$-$C_3$-halogenoalkoxy, $C_1$-$C_3$-alkylthio, or phenyl, phenoxy or phenylthio, each of which is unsubstituted or monosubstituted to penta-substituted, in particular monosubstituted to tri-substituted, by identical or different substituents, the following being selected as phenyl substituents: fluorine, chlorine, bromine, methyl, ethyl, n- or iso-propyl, methoxy, ethoxy, n- or iso-propoxy and trifluoromethyl, Y represents hydrogen, fluorine, chlorine, bromine, methyl, ethyl, methoxy, ethoxy, trifluoromethoxy or trifluoromethyl, Z represents fluorine or chlorine, n represents 0, 1, 2 or 3 and A represents methyl, ethyl, an in each case straight-chain or branched radical from the series comprising propyl, butyl, pentyl, hexyl, heptyl, octyl, nonyl, decyl, halogeno-$C_1$-$C_6$-alkyl, $C_3$-$C_6$-alkenyl, $C_3$-$C_6$-alkinyl, $C_1$-$C_4$-alkoxy-$C_1$-$C_4$-alkyl, $C_1$-$C_4$-alkylthio-$C_1$-$C_4$-alkyl, or represents cycloalkyl which has 3 to 6 ring atoms and which can be interrupted by oxygen, nitrogen or sulphur, or A represents a radical from the series comprising phenyl, benzyl or phenethyl, each of which is unsubstituted or mono-substituted to pentasubstituted, in particular monosubstituted to trisubstituted, by identical or different substituents, selected substituents in each case being: fluorine, chlorine, methyl, ethyl, n- or iso-propyl, methoxy, ethoxy, trifluoromethyl, trifluoromethoxy, or phenoxy or phenylthio, each of which is unsubstituted or monosubstituted to tri-substituted by identical or different substituents from the series comprising fluorine, chlorine, methyl, methoxy, trifluoromethyl and trifluoromethoxy, B represents hydrogen, the group

or the group

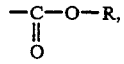

L represents hydrogen, or represents an optionally halogen-substituted straight-chain or branched radical from the series comprising $C_1$-$C_{10}$-alkyl, $C_3$-$C_6$-alkenyl, $C_3$-$C_6$-alkinyl, $C_1$-$C_8$-alkoxy-$C_2$-$C_6$-alkyl, $C_1$-$C_6$-polyalkoxy-$C_2$-$C_6$-alkyl, $C_1$-$C_8$alkylthio-$C_2$-$C_6$-alkyl, cycloalkyl which has 3 to 7 ring atoms and which can be interrupted by 1 to 2 oxygen and/or sulphur atoms, or aryl which is optionally substituted by halogen, $C_1-C_4$-alkyl, $C_1-C_4$-halogenoalkyl, $C_1-C_4$-alkoxy or nitro, M represents hydrogen or a straight-chain or branched radical from the series comprising $C_1-C_{10}$-alkyl, $C_1-C_6$-alkoxyalkyl, or in which A and L or L and M together with the atoms to which they are bonded form a 3 to 7-membered ring which can be saturated or unsaturated and substituted by $C_1-C_6$-alkyl, $C_1-C_4$-alkoxy, $C_1-C_2$-halogenoalkyl or phenyl and/or interrupted by oxygen/sulphur, R represents an optionally halogen-substituted straight-chain or branched radical from the series comprising $C_1-C_{10}$-alkyl, $C_3-C_6$-alkenyl, $C_3-C_6$-alkinyl, $C_1-C_8$-alkoxy-$C_1-C_6$-alkyl, $C_1-C_6$-polyalkoxy-$C_2-C_6$-alkyl, $C_1-C_8$-alkylthio-$C_2-C_6$-alkyl, cycloalkyl which has 3 to 7 ring atoms and which can be interrupted by 1 to 2 oxygen and/or sulphur atoms, or represents aryl which is optionally substituted by halogen, $C_1-C_4$alkyl, $C_1-C_4$-halogenoalkyl, $C_1-C_4$-alkoxy or nitro, and the enantiomeric compounds of the formula with the exception of the compounds: 4-amino-1-cyclopropyl-3-(3-trifluoromethylphenyl)-3-pyrrolin-2-one and 4-amino-1-isopropyl-3-(3-trifluoromethylphenyl)-3-pyrrolin-2-one.

A very particularly preferred group of compounds are those of the formula (I) in which X represents hydrogen, fluorine, chlorine, bromine, methyl, ethyl, methoxy, ethoxy, n- or i-propoxy, trifluoromethyl, trifluoromethoxy, or represents phenyl or phenoxy, each of which is unsubstituted or monosubstituted to trisubstituted by identical or different substituents, selected substituents being the following: fluorine, chlorine, methyl and trifluoromethyl, Y represents hydrogen, fluorine, chlorine, bromine, methyl, methoxy, trifluoromethoxy or trifluoromethyl, n represents 0 and A represents methyl, ethyl, n-propyl, iso-propyl, n-, iso-, sec.- or tert.-butyl, or represents an in each case straight-chain or branched radical from the series comprising pentyl, hexyl, heptyl, octyl, halogeno-$C_1-C_3$-alkyl, allyl, propargyl, methoxymethyl, methoxyethyl, ethoxymethyl, ethoxyethyl, cyclopropyl, cyclopentyl, cyclohexyl, or represents phenyl or benzyl, each of which is unsubstituted or monosubstituted to trisubstituted by identical or different substituents from the series comprising fluorine, chlorine, trifluoromethyl, phenoxy and 4-trifluoromethyl-phenoxy, B represents hydrogen, the group —CO—R or the group

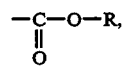

L represents hydrogen or an optionally halogen-substituted straight-chain or branched radical from the series comprising $C_1-C_8$-alkyl, $C_3-C_4$-alkenyl, $C_3-C_4$alkinyl, $C_1-C_6$-alkoxy-$C_2-C_4$-alkyl, $C_1-C_4$-polyalkoxy-$C_2-C_4$-alkyl, $C_1-C_6$-alkylthio-$C_2-C_4$-alkyl, cycloalkyl which has 3 to 6 ring atoms and which can be interrupted by 1 to 2 oxygen and/or sulphur atoms, or aryl which is optionally substituted by fluorine, chlorine, bromine, methyl, ethyl, propyl, iso-propyl, methoxy, ethoxy, trifluoromethyl or nitro, M represents hydrogen or a straight-chain or branched radical from the series comprising $C_1-C_8$-alkyl, $C_1-C_4$-alkoxyalkyl, or in which A and L or L and M together with the atoms to which they are bonded form a 3 to 6-membered ring which can be saturated or monounsaturated, substituted by $C_1-C_4$-alkyl, $C_1-C_2$-alkoxy, trifluoromethyl or phenyl, and/or interrupted by oxygen/sulphur, R represents an optionally halogen-substituted straight-chain or branched radical from the series comprising $C_1-C_8$-alkyl, $C_3-C_4$-alkenyl, $C_3-C_4$-alkinyl, $C_1-C_6$-alkoxy-$C_2-C_4$-alkyl, $C_1-C_4$-polyalkoxy-$C_2-C_4$-alkyl, $C_1-C_6$-alkylthio-$C_2-C_4$-alkyl, cycloalkyl which has 3 to 6 ring atoms and which can be interrupted by 1 to 2 oxygen and/or sulphur atoms, or represents aryl which is optionally substituted by fluorine, chlorine, bromine, methyl, ethyl, propyl, isopropyl, methoxy, ethoxy, trifluoromethyl or nitro, and the enantiomeric compounds of the formula (I) with the exception of the compounds: 4-amino-1-cyclopropyl-3-(3-trifluoromethylphenyl)-3-pyrrolin-2-one and 4-amino-1-isopropyl-3-(3-trifluoromethylphenyl)-3-pyrrolin-2-one.

If, according to the general preparation process (aα), 3-(3-trifluoromethylphenyl)-1-isopropyl-5-methylpyrrolidine-2,4-dione and ammonium acetate are used as starting materials, the course of the process according to the invention can be represented by the following equation:

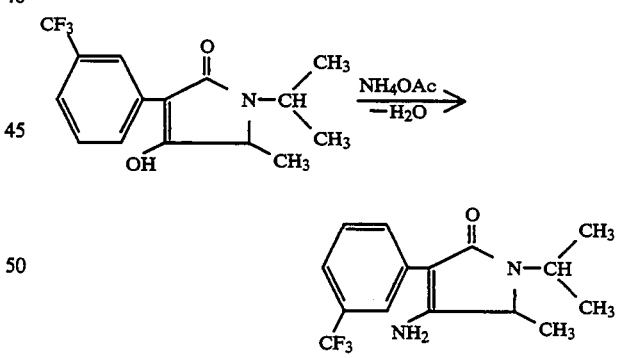

If, according to the general preparation process (aβ), N-(3-trifluoromethylphenylacetyl)-N-methylamino-2-ethylacetonitrile is used, the course of the process according to the invention can be represented by the following equation:

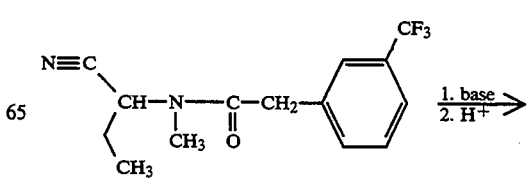

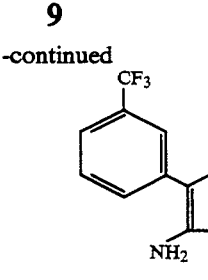

If, according to the general preparation process (bα), 3-(3,4-dichlorophenyl)-1-(4-chlorophenyl)-4-amino-3-pyrrolin-2-one and acetyl chloride are used as starting materials, the course of the process according to the invention can be represented by the following equation:

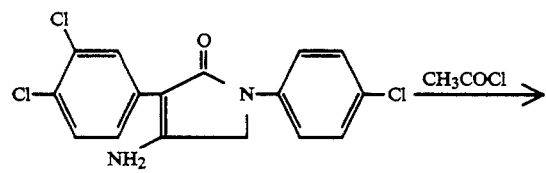

If, according to the general preparation process (bβ), 3-(3-methoxyphenyl)-1-phenyl-5-methyl-4-amino-3-pyrrolin-2-one and 2-ethyl-butyric anhydride are used as starting materials, the course of the process according to the invention can be represented by the following equation:

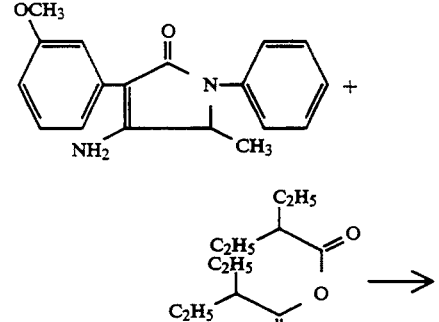

If, according to the general preparation process (c), 3-(3-trifluoromethylphenyl)-1-tert.-butyl-5-methyl-4-amino-3-pyrrolin-2-one and methyl chloroformate are used as starting materials, the course of the process according to the invention can be represented by the following equation:

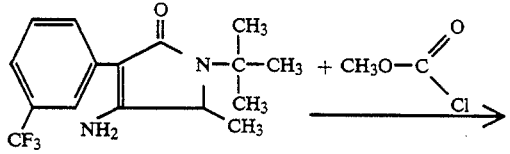

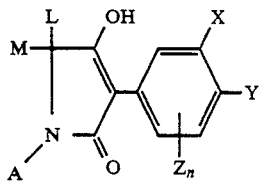

The compounds of the formula (II)

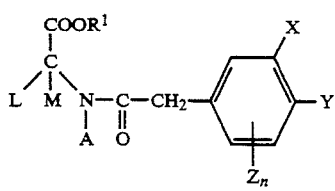

in which A, L, M, X, Y, Z and n have the abovementioned meanings and which are required as starting materials for carrying out process (aα) according to the invention are obtained when N-acylamino acid esters of the formula (VII)

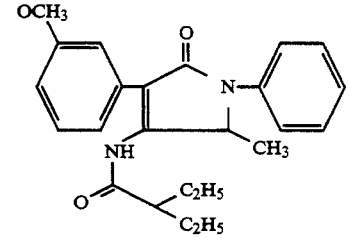

in which
  A, L, M, X, Y, Z and n have the abovementioned meanings and
  $R^1$ represents alkyl, in particular methyl or ethyl, are subjected to intramolecular condensation in the presence of a diluent and in the presence of a base.

Some of the compounds of the formula (VII) are known or can be prepared in a simple manner by customary methods.

For example, N-acylamino acid esters of the formula (VII) are obtained when acylamino acid esters of the formula (VIII)

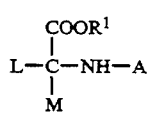

in which
  $R^1$ represents hydrogen or alkyl, in particular methyl or ethyl, and
  A, L and M have the abovementioned meanings, are acylated with phenylacetic acid halides of the formula (IX)

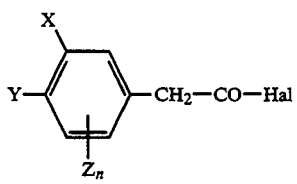

in which

Hal represents halogen, in particular fluorine, chlorine or bromine, and

X, Y, Z and n have the abovementioned meanings, in the customary manner (cf. Chem. Rev. 52 (1953) 237–416 and Organikum [Laboratory Practical in Organic Chemistry], 9th Edition, 446 (1970), VEB Deutscher Verlag der Wissenschaften), or when N-acylamino acids of the formula (II) in which $R^1$ represents hydrogen, are esterilied in the customary manner (cf. Chem. Ind. (London) 1568 (1968)).

Compounds of the formula (VII) in which $R^1$ represents hydrogen can also be prepared, for example, from phenylacetic acid halides of the formula (IX) and amino acids.

Compounds of the formula (VIII) can be obtained from α-halogeno carboxylic acids or α-halogeno carboxylates and amines or anilines, respectively, by processes known from the literature (Advanced Organic Chemistry, J. March, pp. 377, Mc Graw-Hill Inc. (1977)).

The phenylacetic acid halides of the formula (IX) are known compounds of organic chemistry.

Some of the compounds of the formula (II) are compounds which are known from EP-A-0,415,185. Compounds which were hitherto unknown are also part of the claim (see Table 1).

TABLE 1

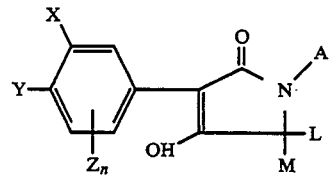

(II)

| Ex. No. | X | Y | $Z_n$ | M | L | A |
|---|---|---|---|---|---|---|
| 1 | $CF_3$ | H | — | H | H | 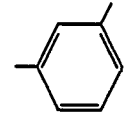 |
| 2 | $CF_3$ | H | — | $CH_3$ | H | $-CH_2-CH_2OCH_3$ |
| 3 | $CF_3$ | H | — | $CH_3$ | H | $i-C_3H_7$ |
| 4 | $CF_3$ | H | — | $CH_3$ | H | $CH_3$ |
| 5 | H | H | — | $CH_3$ | H | $i-C_3H_7$ |
| 6 | $CF_3$ | H | — | $CH_3$ | H | 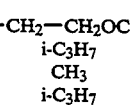 |
| 7 | $CF_3$ | H | — | $CH_3$ | H | $C_2H_5$ |
| 8 | $CF_3$ | H | — | $CH_3$ | H | 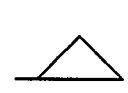 |
| 9 | $CF_3$ | H | — | $CH_3$ | H | 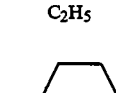 |
| 10 | $CF_3$ | H | — | $CH_3$ | H | $-\overset{\underset{\displaystyle CH_3}{\mid}}{CH}-CH_2-CH_3$ |
| 11 | $CF_3$ | H | — | $CH_3$ | H | 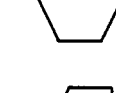 |
| 12 | $CF_3$ | H | — | H | | $-CH_2-CH_2-CH_2-CH_2-$ |
| 13 | H | Cl | — | H | | $-CH_2-S-CH_2-CH_2-$ |
| 14 | H | Cl | — | H | | $-CH_2-S-CH_2-$ |
| 15 | H | Cl | — | H | | $-CH_2-CH_2-S-CH_2-$ |
| 16 | Cl | Cl | — | H | $CH_3$ | $CH_3$ |
| 17 | Cl | Cl | — | H | | $-CH_2-S-CH_2-CH_2-$ |
| 18 | Cl | Cl | — | H | $CH_3$ | $i-C_3H_7$ |

TABLE 1-continued
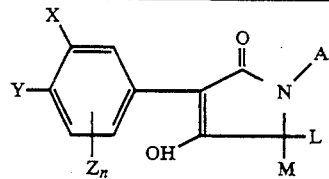
(II)
| Ex. No. | X | Y | $Z_n$ | M | L | A |
|---|---|---|---|---|---|---|
| 19 | Cl | Cl | — | H | $CH_3$ | cyclopentyl |
| 20 | Cl | Cl | — | H | $C_2H_5$ | $CH_3$ |
| 21 | Cl | Cl | — | $CH_3$ | H | cyclopropyl |
| 22 | Cl | Cl | — | $CH_3$ | H | $C_2H_5$ |
| 23 | Cl | Cl | — | $CH_3$ | H | $i\text{-}C_4H_9$ |
| 24 | Br | H | — | $CH_3$ | H | $CH_3$ |
| 25 | $CF_3$ | H | — | $CH_3$ | H | $C_6H_5$ |
| 26 | $CF_3$ | H | — | $CH_3$ | H | 4-F-C₆H₄ |
| 27 | $CF_3$ | H | — | $CH_3$ | H | 3-CF₃-C₆H₄ |
| 28 | $CF_3$ | H | — | $CH_3$ | H | 4-F-C₆H₄ |
| 29 | $CF_3$ | H | — | $CF_3$ | H | 3,4-di-F-C₆H₃ |
| 30 | H | 2,6-diCl-4-CF₃-phenoxy | — | H | $CH_3$ | $C_6H_5$— |
| 31 | 2,6-diCl-4-CF₃-phenoxy | H | — | H | $CH_3$ | $C_6H_5$— |
| 32 | H | H | — | H | $CH_3$ | 3-F-C₆H₄ |

TABLE 1-continued (II)

Structure: X, Y on benzene ring with $Z_n$; ring attached to C=C(OH)–C(L)(M)–N(A)–C=O (pyrrolinone-type)

| Ex. No. | X | Y | $Z_n$ | M | L | A |
|---|---|---|---|---|---|---|
| 33 | $CF_3$ | Cl | — | H | —(CH$_2$)$_4$— (spans L and A) | |
| 34 | $CF_3$ | H | — | H | $CH_3$ | $H_3CO-CH_2-CHCH_3-$ |
| 35 | $CF_3$ | H | — | H | –CH$_2$CH$_2$–C$_6$H$_5$ | $CH_3$ |
| 36 | $CF_3$ | H | — | H | –CH$_2$CH$_2$–(4-Cl-C$_6$H$_4$) | $CH_3$ |
| 37 | $CF_3$ | H | — | H | –CH$_2$CH$_2$–(4-CH$_3$-C$_6$H$_4$) | $CH_3$ |
| 38 | $CF_3$ | H | — | H | –CH$_2$CH$_2$–(2-Cl-C$_6$H$_4$) | $CH_3$ |
| 39 | $CF_3$ | H | — | H | –CH$_2$CH$_2$–(4-Cl-C$_6$H$_4$) | $CH_3$ |
| 40 | $CF_3$ | H | — | H | –CH$_2$CH$_2$–(4-CF$_3$-C$_6$H$_4$) | $CH_3$ |
| 41 | $CF_3$ | H | — | H | $C_6H_5$ | $CH_3$ |
| 42 | $CF_3$ | H | — | H | 3-Cl-C$_6$H$_4$ | $CH_3$ |
| 43 | $CF_3$ | H | — | H | 4-CH$_3$-C$_6$H$_4$ | $CH_3$ |
| 44 | $CF_3$ | H | — | H | 3-Cl-C$_6$H$_4$ | $CH_3$ |
| 45 | $CF_3$ | H | — | H | 4-CH$_3$O-C$_6$H$_4$ | $CH_3$ |

TABLE 1-continued (II)

| Ex. No. | X | Y | $Z_n$ | M | L | A |
|---|---|---|---|---|---|---|
| 46 | CF$_3$ | H | — | H | 4-Cl-C$_6$H$_4$ | CH$_3$ |
| 47 | CF$_3$ | H | — | CH$_3$ | H | CH$_2$-iPr |
| 48 | CF$_3$ | H | — | H | C$_2$H$_5$ | C$_2$H$_5$ |
| 49 | CF$_3$ | H | — | CH$_3$ | H | —CH(CH$_3$)$_2$ |
| 50 | CF$_3$ | H | — | CH$_3$ | H | —C(CH$_3$)$_2$—CH$_2$—C(CH$_3$)$_3$ |
| 51 | CF$_3$ | H | — | CH$_3$ | H | 2,4,6-tri-CH$_3$-C$_6$H$_2$ |
| 52 | CF$_3$ | H | — | CH$_3$ | H | cyclopentyl |
| 53 | CF$_3$ | H | — | CH$_3$ | H | —CH$_2$CH$_2$—O—CH$_3$ |
| 54 | CF$_3$ | H | — | CH$_3$ | H | —CH(CF$_3$)(CH$_3$) |
| 55 | CF$_3$ | H | — | CH$_3$ | H | C$_6$H$_5$ |
| 56 | CF$_3$ | H | — | CH$_3$ | H | 2-Cl-C$_6$H$_4$ |
| 57 | CF$_3$ | H | — | CH$_3$ | H | 2,4-diCl-C$_6$H$_3$ |
| 58 | CF$_3$ | H | — | CH$_3$ | H | 2,6-diCl-C$_6$H$_3$ |
| 59 | CF$_3$ | H | — | CH$_3$ | H | 4-CF$_3$-C$_6$H$_4$ |

TABLE 1-continued
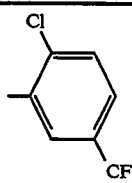
(II)
| Ex. No. | X | Y | $Z_n$ | M | L | A |
|---|---|---|---|---|---|---|
| 60 | $CF_3$ | H | — | $CH_3$ | H | 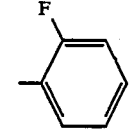 |
| 61 | $CF_3$ | H | — | $CH_3$ | H | 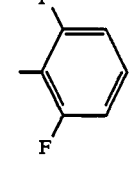 |
| 62 | $CF_3$ | H | — | $CH_3$ | H | 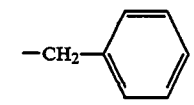 |
| 63 | $CF_3$ | H | — | $CH_3$ | H | $-CH_2-C(CH_3)_3$ |
| 64 | $CF_3$ | H | — | $CH_3$ | H | $-CH(CH_3)-C(CH_3)_3$ |
| 65 | $CF_3$ | H | — | $CH_3$ | H | 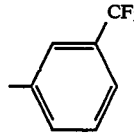 |
| 66 | H | H | — | $CH_3$ | H |  |
| 67 | H | H | — | $CH_3$ | H | 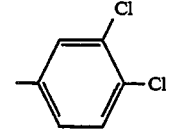 |
| 68 | $CF_3$ | H | — | $CH_3$ | H | $-CH(CH_3)-CH(CH_3)_2$ |
| 69 | $CF_3$ | H | — | $CH_3$ | H | 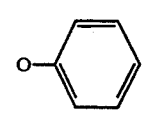 |
| 70 | 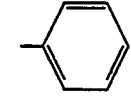 | H | — | $CH_3$ | H | 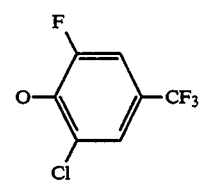 |
| 71 | H | 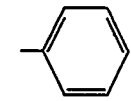 | — | $CH_3$ | H | 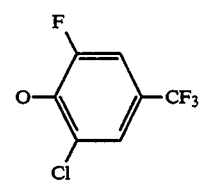 |

TABLE 1-continued
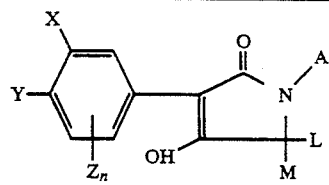
(II)
| Ex. No. | X | Y | Z$_n$ | M | L | A |
|---|---|---|---|---|---|---|
| 72 | CF$_3$ | H | — | CH$_3$ | H | 3-chlorophenyl |
| 73 | H | H | — | CH$_3$ | H | phenyl |
| 74 | H | H | — | CH$_3$ | H | 2,4-difluorophenyl |
| 75 | CF$_3$ | H | — | CH$_3$ | H | 4-phenoxyphenyl |
| 76 | CF$_3$ | H | — | CH$_3$ | H | 4-(4-trifluoromethylphenoxy)phenyl |
| 77 | H | H | — | CH$_3$ | H | 2-chlorophenyl |
| 78 | F | F | — | CH$_3$ | H | 3-trifluoromethylphenyl |
| 79 | CF$_3$ | H | — | CH$_3$ | H | 2-trifluoromethyl-4-phenoxyphenyl |
| 80 | Cl | Cl | — | CH$_3$ | H | —CH$_2$—CH(CH$_3$)$_2$ |
| 81 | Cl | Cl | — | CH$_3$ | H | —CH(CH$_3$)—C$_2$H$_5$ |
| 82 | Cl | Cl | — | CH$_3$ | H | cyclopentyl |

TABLE 1-continued

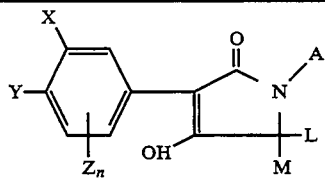

(II)

| Ex. No. | X | Y | $Z_n$ | M | L | A |
|---|---|---|---|---|---|---|
| 83 | Cl | Cl | — | CH₃ | H | cyclohexyl |
| 84 | Cl | Cl | — | CH₃ | H | —CH₂CH₂—O—CH₃ |
| 85 | Cl | Cl | — | CH₃ | H | —CH(CH₃)₂ |
| 86 | Cl | Cl | — | CH₃ | H | —CH₃ |
| 87 | Br | H | — | CH₃ | H | —CH₂—CH(CH₃)₂ |
| 88 | Br | H | — | CH₃ | H | —CH(CH₃)—C₂H₅ |
| 89 | Br | H | — | CH₃ | H | cyclopropyl |
| 90 | Br | H | — | CH₃ | H | cyclopentyl |
| 91 | Br | H | — | CH₃ | H | cyclohexyl |
| 92 | Br | H | — | CH₃ | H | —CH₂CH₂—O—CH₃ |
| 93 | Br | H | — | CH₃ | H | —CH(CH₃)₂ |
| 94 | Br | H | — | CH₃ | H | —C₂H₅ |
| 95 | Br | H | — | CH₃ | H | —CH₃ |

The process for the preparation of compounds of the formula (II) is characterised in that compounds of the formula (VII) are subjected to intramolecular condensation in the presence of bases.

Diluents which can be employed in this process according to the invention are all customary inert organic solvents. The following can preferably be used: hydrocarbons such as toluene and xylene, furthermore ethers such as dibutyl ether, tetrahydrofuran, dioxane, glylcol dimethyl ether and diglycol dimethyl ether, moreover polar solvents such as dimethyl sulphoxide, sulpholane, dimethylformamide, N-methyl-pyrrolidone, and also alcohols such as ethanol, methanol, isobutanol, sec.-butanol and tert.-butanol.

Deprotonating agents which can be employed for carrying out this process according to the invention are all customary proton acceptors. The following can preferably be used: the oxides, hydroxides and carbonates of alkali metals and alkaline earth metals such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, *Adogen 464 or TDA 1. Other substances which can be employed are amides and hydrides of alkali metals and alkaline earth metals such as sodium amide, sodium hydride and calcium hydride, and moreover also alkali metal alcoholates such as sodium methylate and potassium tert.-butylate.

*Adogen 464=methyltrialkyl(C₈-C₁₀)ammonium chloride TDA 1=tris(methoxyethoxyethyl)amine When carrying out this process according to the invention, the reaction temperatures can be varied within a substantial range. In general, the process is carried out at temperatures between 0° C. and 250° C., preferably between 50° C. and 150° C.

The process according to the invention is generally carried out under atmospheric pressure.

When carrying out this process according to the invention, the reactants of the formula (VII) and the deprotonating bases are generally employed in approximately equimolar amounts. However, it is also possible to use one or the other component in a larger excess (up to 3 moles).

Diluents which are preferably suitable for carrying out process (aα) according to the invention are inert organic solvents. These include, in particular, aliphatic, alicyclic or aromatic, optionally halogenated hydrocarbons such as, for example, benzine, ligroine, benzene, toluene, xylene, chlorobenzene, petroleum ether, pentane, hexane, heptane, cyclohexane, dichloromethane, chloroform, carbon tetrachloride, ethers such as diethyl ether, dioxane, tetrahydrofuran or ethylene glycol dimethyl ether or ethylene glycol diethyl ether, ketones such as acetone or butanone, nitriles such as acetonitrile or propionitrile, amides, such as dimethylformamide, dimethylacetamide, N-methylformanilide, N-methylpyrrolidone or hexamethylphosphoric triamide, or esters, such as ethyl acetate. A suitable excess of the amines of the formula (IV) in liquid form can also be employed as solvent.

If appropriate, process (aα) according to the invention is carried out in the presence of a dehydrating agent. The following are preferably used as dehydrating agents:

molecular sieves or catalytic amounts of, for example, p-toluenesulphonic acid. A favourable procedure is removal of the water during the reaction by azeotropic distillation.

When carrying out process (aα) according to the invention, the reaction temperatures can be varied within a substantial range. In general, the process is carried out at temperatures between 0° C. and 300° C., preferably at temperatures between 20° C. and 250° C.

Process (aα) according to the invention is customarily carried out under atmospheric pressure. However, the process can also be carried out under increased pressure.

For carrying out process (aα) according to the invention, 1 to 30 moles, preferably 1 to 10 moles, of ammonia or an ammonium salt and, if appropriate, 1 to 5 moles of dehydrating agent are generally employed per mole of compound of the formula (II) in which B represents hydroxyl. The reaction is carried out and the reaction products are worked up and isolated analogously to generally known processes.

Process (aα) is characterised in that compounds of the formula (III) are subjected to intramolecular condensation in the presence of bases.

Diluents which can be employed in process (aβ) according to the invention are all customary inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents such as dimethyl sulphoxide, sulpholane, dimethylformamide, N-methyl-pyrrolidone, and also alcohols such as ethanol, methanol, isobutanol, sec.-butanol and tert.-butanol.

Deprotonating agents which can be employed for carrying out process (aβ) according to the invention are all customary proton acceptors. The following can preferably be used: the oxides, hydroxides and carbonates of alkali metals and alkaline earth metals such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, *Adogen 464 or TDA 1. Other substances which can be employed are amides and hydrides of alkali metals and alkaline earth metals such as sodium amide, sodium hydride and calcium hydride, and moreover also alkali metal alcoholates such as sodium methylate and potassium tert.-butylate.

*Adogen 464=methyltrialkyl(C$_8$–C$_{10}$)ammonium chloride TDA 1=tris(methoxyethoxyethyl)amine When carrying out process (aβ) according to the invention, the reaction temperatures can be varied within a substantial range. In general, the process is carried out at temperatures between 0° C. and 250° C., preferably between 50° C. and 150° C.

The process (aβ) is generally carried out under atmospheric pressure.

When carrying out process (aβ), the reactants of the formula (III) and the deprotonating bases are generally employed in approximately equimolar amounts. However, it is also possible to use one or the other component in a larger excess (up to 3 moles).

Process (bα) is characterised in that compounds of the formula (Ia) are reacted with carboxylic acid halides of the formula (IV).

When the acid halides are used, then diluents which can be employed in process (bα) according to the invention are all solvents which are inert to these compounds. The following can preferably be used: hydrocarbons such as benzine, benzene, toluene, xylene and tetraline, furthermore halogeno hydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, and additionally sulphoxides, such as dimethyl sulphoxide and sulpholane. If stability to hydrolysis of the acid halide permits, the reaction can also be carried out in the presence of water. However, it is also possible to carry out the process without solvent.

If the corresponding carboxylic acid halides are used, then suitable acid-binding agents in the reaction by process (bα) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate. However, acid-binding agents can also be dispensed with.

The reaction temperatures in process (aα) according to the invention can be varied within a substantial range, even when carboxylic acid halides are used. The process is generally carried out at temperatures between −20° C. and +200° C., preferably between 0° C. and 150° C.

When carrying out process (bα) according to the invention, the starting materials of the formula (Ia) and the carboxylic acid halide of the formula (IV) are generally employed in approximately equivalent amounts. However, it is also possible to employ the carboxylic acid chloride in a larger excess (up to 20 moles). Working-up is carried out by customary methods.

Process (bβ) is characterised in that compounds of the formula (Ia) are reacted with carboxylic acid hydrides of the formula (V).

If carboxylic anhydrides are used as reactant of the formula (V) in process (bβ) according to the invention, then the diluents which are preferably used are those which are also preferably suitable when acid halides are used. Besides, an excess of carboxylic acid hydride can also act simultaneously as the diluent.

The reaction temperatures in process (bβ) according to the invention can be varied within a substantial range, even when carboxylic anhydrides are used. In general, the process is carried out at temperatures between −20° C. and 200° C., preferably between 0° C. and 150° C.

When carrying out process (bβ) according to the invention, the starting materials of the formula (Ia) and the carboxylic anhydride of the formula (V) are generally employed in approximately equivalent amounts. However, it is also possible to employ the carboxylic anhydride in a larger excess (up to 20 moles). Working-up is carried out by customary methods.

In general, a procedure is followed in which diluents and excess carboxylic anhydride and the carboxylic acid which forms are removed by distillation or by washing with an organic solvent or with water.

Process (c) is characterised in that compounds of the formula (Ia) are reacted with chloroformates of the formula (VI).

If the corresponding chloroformates are used, then suitable acid-binding agents in the reaction by process (c) according to the invention are all customary acid acceptors. The following can preferably be used: tertiary amines such as triethylamine, pyridine, DABCO, DBU, DBN, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

When the chloroformates are used, then diluents which can be employed in process (c) according to the invention are all solvents which are inert to these compounds. The following can preferably be used: hydrocarbons such as benzine, benzene, toluene, xylene and tetraline, furthermore halogeno hydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylates such as ethyl acetate, and also strongly polar solvents such as dimethyl sulphoxide and sulpholane. However, the process can also be carried out without solvent.

When the chloroformates are used as carboxylic acid derivatives of the formula (VI), the reaction temperatures for carrying out process (c) according to the invention can be varied within a substantial range. If the process is carried out in the presence of a diluent and of an acid-binding agent, then the reaction temperatures are generally between $-20°$ C. and $+250°$ C., preferably between $0°$ C. and $150°$ C.

Process (c) according to the invention is generally carried out under atmospheric pressure.

When carrying out process (c) according to the invention, the starting materials of the formula (Ia) and the corresponding chloroformate of the formula (VI) are generally used in approximately equivalent amounts. However, it is also possible to employ one or the other component in a larger excess (up to 10 moles). Working-up is then carried out by customary methods. In general, a procedure is followed in which precipitated salts are removed and the reaction mixture which remains is concentrated by removing the diluent in vacuo.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the qenera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants. The compounds are suitable, depending on the concentration, for the total combating of weeds, for example on industrial plants and railway lines, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are very suitable for the selective combating of mono- and dicotyledon weeds in mono- and dicotyledon crops in the pre- and post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the forth of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as a mixture with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmediphamand propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribehuron-methyl; thiocarbanates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazol, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

EXAMPLE 1

Synthesis of the acylamino acid ester (VIII)

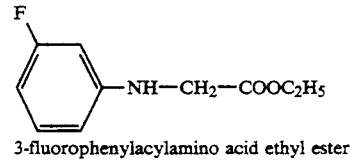

3-fluorophenylacylamino acid ethyl ester

MW 197

22.2 g (0.2 mol) of 3-fluoroaniline were introduced into 100 ml of xylene and 20.2 g (0.2 mol) of triethylamine are added. The mixture is then cooled to 10°–20° C., during which process 33.4 g (0.2 mol) of ethyl bromoacetate is added dropwise. When this procedure has ended, the mixture is refluxed for 8 hours and then allowed to cool, and the xylene is removed in vacuo. The residue is treated with 100 ml of water, and the mixture extracted twice using 60 ml portions of methylene chloride and dried over magnesium sulphate. Finally, the magnesium sulphate is removed by filtration, the solution is concentrated in vacuo, and 37.6 g (95.4% of theory) of 3-fluorophenylacylamino acid ethyl ester are obtained in the form of a yellow oil which is identified by NMR spectroscopy.

EXAMPLE 2

Synthesis of the N-acylamino acid esters (VII)

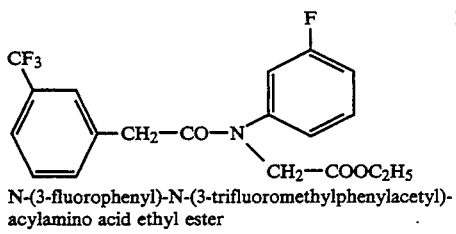

MW 383

N-(3-fluorophenyl)-N-(3-trifluoromethylphenylacetyl)-acylamino acid ethyl ester 19.7 g (0.1 mol) of 3-fluorophenylacylamino acid ethyl ester and 10.1 g (0.1 mol) of triethylamine are introduced into 150 ml of tetrahydrofuran. The mixture is cooled to 2° to 6° C., and 22.3 g (0.1 mol) of 3-trifluoromethylphenylacetic acid chloride in 20 m 1 of tetrahydrofuran are then added dropwise.

When the procedure has ended, stirring of the mixture is continued for 30 minutes at room temperature, the reaction solution is introduced into 700 ml of ice-water, the mixture is treated with 100 ml of 1-normal HCl and extracted twice using 150 ml portions of methylene chloride, and the combined organic phases are dried over magnesium sulphate.

After the magnesium sulphate has been filtered off, the solvent is removed in vacuo, and 37 g (96.6% of theory) of N-(3-fluorophenyl)-N-(3-trifluoromethylphenylacetyl)-acylamino acid ethyl ester, which is identified by NMR spectroscopy, are obtained.

EXAMPLE 3

Synthesis of the intermediates (II)

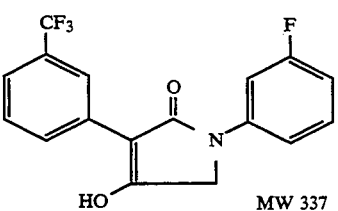

(II-1)

MW 337

3-(3-trifluoromethylphenyl)-1-(3-fluorophenyl)-pyrrolidine-2,4-dione 3.77 g (0.126 mol) of sodium hydride are introduced into 90 ml of absolute toluene, and 37 g (0.097 mol) of N-(3-fluorophenyl)-N-(3-trifluoromethylphenylacetyl)-acylamino acid ethyl ester, also dissolved in 100 ml of absolute toluene, are added dropwise at 90° C. to 100° C. The mixture is subsequently refluxed for one hour after the reaction, before being cooled to 3° C. to 5° C. (ice-bath mixture) and 30 ml of ethanol, 75 ml of water and 20 ml of concentrated hydrochloric acid are added dropwise. The white precipitate which separates out during this process is finally filtered off, washed with acetone and dried.

27.2 g (83.4% of theory) of 3-(3-trifluoromethylphenyl)- 1-(3-fluorophenyl)-pyrrolidine-2,4-dione of melting point 208° C. to 209° C., which is identified by NMR spectroscopy, are obtained.

The products of the formula (II) which are subsequently listed in Table 2 are obtained analogously to the above-described synthesis of the intermediates (II) and taking into consideration the information in the description of process (a) according to the invention.

TABLE 2

(II)

| Ex. No. | X | Y | Z | n | M | L | A | Melting point/°C. |
|---------|-----|---|---|---|-----|---|------------------------|-------------------|
| II-2    | CF₃ | H | — | — | CH₃ | H | —CH₂—CH₂OCH₃           | 138               |
| II-3    | CF₃ | H | — | — | CH₃ | H | i-C₃H₇                 | 189               |
| II-4    | CF₃ | H | — | — | CH₃ | H | CH₃                    | 207               |
| II-5    | H   | H | — | — | CH₃ | H | i-C₃H₇                 | 180               |
| II-6    | H   | H | — | — | CH₃ | H | cyclopropyl            | 207               |
| II-7    | CF₃ | H | — | — | CH₃ | H | C₂H₅                   | 205               |
| II-8    | CF₃ | H | — | — | CH₃ | H | cyclohexyl             | 218               |
| II-9    | CF₃ | H | — | — | CH₃ | H | cyclopentyl            | 191               |
| II-10   | CF₃ | H | — | — | CH₃ | H | —CH(CH₃)—CH₂—CH₃       | 168               |

TABLE 2-continued

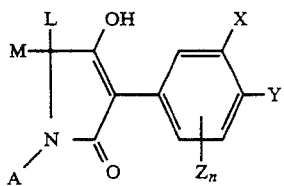
(II)

| Ex. No. | X | Y | Z | n | L | M | A | Melting point/°C. |
|---|---|---|---|---|---|---|---|---|
| II-11 | CF$_3$ | H | — | — | CH$_3$ | H | cyclopropyl | 218 |
| II-12 | CF$_3$ | H | — | — | H | —CH$_2$—CH$_2$—CH$_2$—CH$_2$— | | >220 |
| II-13 | H | Cl | — | — | H | —CH$_2$—S—CH$_2$—CH$_2$— | | 230 |
| II-14 | H | Cl | — | — | H | —CH$_2$—S—CH$_2$— | | 183 |
| II-15 | H | Cl | — | — | H | —CH$_2$—CH$_2$—S—CH$_2$— | | 230 |
| II-16 | Cl | Cl | — | — | H | CH$_3$ | CH$_3$ | 233 |
| II-17 | Cl | Cl | — | — | H | —CH$_2$—S—CH$_2$—CH$_2$— | | 230 |
| II-18 | Cl | Cl | — | — | H | CH$_3$ | i-C$_3$H$_7$ | 202 |
| II-19 | Cl | Cl | — | — | H | CH$_3$ | cyclopentyl | >220 |
| II-20 | Cl | Cl | — | — | H | C$_2$H$_5$ | CH$_3$ | 220 |
| II-21 | Cl | Cl | — | — | H | CH$_3$ | cyclopropyl | >220 |
| II-22 | Cl | Cl | — | — | H | CH$_3$ | C$_2$H$_5$ | 200 |
| II-23 | Cl | Cl | — | — | H | CH$_3$ | i-C$_4$H$_9$ | 196 |
| II-24 | Br | H | — | — | H | CH$_3$ | CH$_3$ | 201 |
| II-25 | CF$_3$ | H | — | — | H | CH$_3$ | C$_6$H$_5$ | 216 |
| II-26 | CF$_3$ | H | — | — | H | CH$_3$ | 4-Cl-C$_6$H$_4$— | 112 |
| II-27 | CF$_3$ | H | — | — | H | CH$_3$ | 3-CF$_3$-C$_6$H$_4$— | 201 |
| II-28 | CF$_3$ | H | — | — | H | CH$_3$ | 4-F-C$_6$H$_4$— | 195 |
| II-29 | CF$_3$ | H | — | H | CH$_3$ | 3,4-F$_2$-C$_6$H$_3$— | | 216–217 |
| II-30 | H | 3-F-4-(2-Cl-4-CF$_3$-C$_6$H$_3$-O)— | — | H | CH$_3$ | C$_6$H$_5$— | | 249 |

TABLE 2-continued
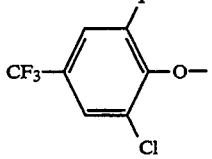
(II)
| No. | L | M | Z_n | X | Y | A | mp |
|---|---|---|---|---|---|---|---|
| II-31 | 4-CF$_3$-2-F-6-Cl-phenoxy | H | — | H | CH$_3$ | C$_6$H$_5$ | 77 |
| II-32 | H | H | — | H | CH$_3$ | 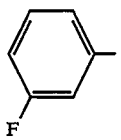 (3-F-C$_6$H$_4$) | 239–240 |
| II-33 | CF$_3$ | Cl | — | H | —(CH$_2$)$_4$— | | 244 |
| II-34 | CF$_3$ | H | — | H | CH$_3$ | H$_3$CO—CH$_2$—CHCH$_3$— | 210 |
| II-35 | CF$_3$ | H | — | H | 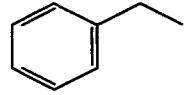 | CH$_3$ | 154–156 |
| II-36 | CF$_3$ | H | — | H | 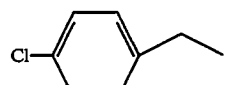 | CH$_3$ | 148–150 |
| II-37 | CF$_3$ | H | — | H | 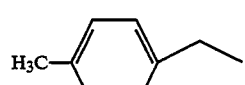 | CH$_3$ | 183–185 |
| II-38 | CF$_3$ | H | — | H | 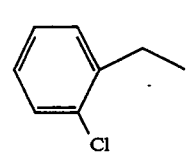 | CH$_3$ | 138–140 |
| II-39 | CF$_3$ | H | — | H | 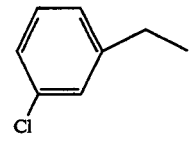 | CH$_3$ | 123–125 |
| II-40 | CF$_3$ | H | — | H | 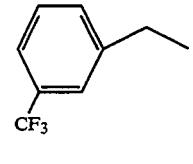 | CH$_3$ | 139–141 |
| II-41 | CF$_3$ | H | — | H | C$_6$H$_5$ | CH$_3$ | 216–218 |
| II-42 | CF$_3$ | H | — | H | 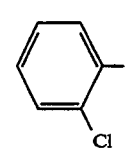 | CH$_3$ | 176–178 |

TABLE 2-continued (II)

| Ex. No. | X | Y | $Z_n$ | M | L | A | Melting point/°C. |
|---|---|---|---|---|---|---|---|
| II-43 | $CF_3$ | H | — | H | H | 4-methylphenyl ($H_3C$-C$_6$H$_4$-) | 221–223 |
| II-44 | $CF_3$ | H | — | H | H | 3-chlorophenyl | 237–239 |
| II-45 | $CF_3$ | H | — | H | 4-methoxyphenyl ($H_3CO$-C$_6$H$_4$-) | $CH_3$ | 204–206 |
| II-46 | $CF_3$ | H | — | H | 4-chlorophenyl (Cl-C$_6$H$_4$-) | $CH_3$ | 200–203 |
| II-47 | $CF_3$ | H | — | $CH_3$ | H | $CH_2$-iPr | 178 |
| II-48 | $CF_3$ | H | — | H | $C_2H_5$ | $C_2H_5$ | 168 |
| II-49 | H | H | — | H | H | 4-fluorophenyl | 250 |
| II-50 | $CF_3$ | H | — | H | H | 2-methylphenyl | 223 |
| II-51 | $CF_3$ | H | — | H | H | 3-methylphenyl | 248 |
| II-52 | $CF_3$ | H | — | H | H | 4-methylphenyl | 250 |
| II-53 | H | $CH_3$ | — | H | H | 4-fluorophenyl | 250 |
| II-54 | H | F | — | H | H | 2-methylphenyl ($H_3C$-C$_6$H$_4$-) | 250 |

TABLE 2-continued (II)

| No. | | | | X | Y | A | m.p. |
|---|---|---|---|---|---|---|---|
| II-55 | H | F | — | H | H | (phenyl) | 250 |
| II-56 | F | H | — | H | H | (3-methylphenyl) | 248 |
| II-57 | F | H | — | H | H | (4-methylphenyl) | 248 |
| II-58 | F | H | — | H | H | (3-CF$_3$-phenyl) | 247 |
| II-59 | F | H | — | H | H | (phenyl) | 235 |
| II-60 | CF$_3$ | H | — | H | H | C$_3$H$_7$iso | 210 |
| II-61 | (2-F-6-Cl-4-CF$_3$-phenoxy) | H | — | H | H | (3-CF$_3$-phenyl) | 205–206 |
| II-62 | (2-F-6-Cl-4-CF$_3$-phenoxy) | H | — | H | H | (phenyl) | 226 |
| I-63 | H | H | — | H | H | (3-F-phenyl) | 230–232 |
| I-64 | CF$_3$ | H | — | CH$_3$ | H | (3-F-phenyl) | 208–209 |
| I-65 | Cl | H | — | H | H | (3-CF$_3$-phenyl) | 235 |

TABLE 2-continued (II)

|  | X | Y | Z | n | A | mp |
|---|---|---|---|---|---|---|
| I-66 | Cl | H | — | H | H | 3-chlorophenyl | 243 |
| I-67 | Cl | H | — | H | H | 3,4-dichlorophenyl | 250 |
| I-68 | Cl | H | Cl | — | H | H | phenyl | 265–270 |
| I-69 | $CF_3$ | H | — | $CH_3$ | H | $-CH_2CH_2OCH_3$ | 123–124 |
| I-70 | $CF_3$ | H | — | $CH_3$ | H | $-CH_2-CH_2-$phenyl | 189–191 |
| I-71 | $CF_3$ | H | — | $CH_3$ | H | $-CH_2-$phenyl | 123–125 |
| I-72 | $CF_3$ | H | — | H | H | $-CH_2-CH_2-S-CH_2-$ | 224–226 |
| I-73 | $CF_3$ | H | — | H | H | $-CH_2-CH_2-CH_2-$ | 234–236 |
| I-74 | $CF_3$ | H | — | $CH_3$ | H | $-CH_2-C(CH_3)_3$ | 215–218 |
| I-75 | $CF_3$ | H | — | H |  | $-CH_2-$cyclopentyl(methyl) | 267–270 |
| I-76 | $CF_3$ | H | — | — | — | $-CH_2CH_2-$phenyl | 215–217 |

EXAMPLE 4

Synthesis of the 4-amino-3-arylpyrrolinone derivatives of the formula (Ia)

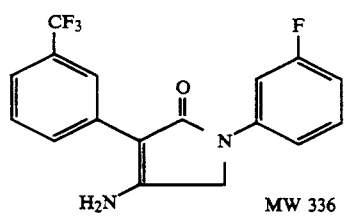

(Ia-1)

4-amino-1-(3-fluorophenyl)-3-(3-trifluoromethylphenyl)-  
MW 336  
pyrrolin-2-one

Process aα

3.77 g (0.01 mol) of 3-(3-trifluoromethylphenyl)-1-(3-fluorophenyl)-pyrrolidine-2,4-dione (II-1) are introduced into 80 ml of xylene, and the mixture is treated with 5 ml of glacial acetic acid and 2 ml of 25% strength aqueous ammonia solution and subsequently refluxed for 6 hours in a water separator. After in each case 2 hours, another 5 ml of glacial acetic acid and 2 ml of ammonia solution are added, so that finally a total of 15 ml of glacial acetic acid and 6 ml of ammonia solution were added. After the last addition, the mixture is refluxed for another hour in a water separator before removing the volatile components in vacuo. The residue is taken up in 50 ml of water, the mixture is extracted three times using 80 ml portions of methylene chloride, and the combined organic phases are washed once with water, dried over magnesium sulphate and concentrated in vacuo. The crystalline residue obtained during this process is stirred with petroleum ether/methylene chloride (1:1), and the white precipitate is filtered off.

3.2 g (73% of theory) of 4-amino-1-(3-fluorophenyl)3-(3-trifluorophenyl)-pyrrolin-2-one of melting point 201°–203° C. are obtained.

The compound is identified by NMR and MS spectroscopy. In individual cases, the crude produce must be chromatographed over silica gel using toluene/acetone (1:1) as eluent, which may reduce the yields to 45 to 75%.

The end products of the formula (Ia) in which B represents hydrogen and which are listed below in Table 3 are obtained analogously to Example 4 and taking into consideration the information in the description of process (a) according to the invention.

TABLE 3

(Ia)

| Ex. No. | X | Y | Z | n | M | L | A | Melting point/°C. |
|---|---|---|---|---|---|---|---|---|
| Ia-2 | $CF_3$ | H | — | — | $CH_3$ | H | $CH_3$ | 130 |
| Ia-3 | H | H | — | — | $CH_3$ | H | 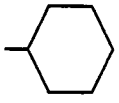 | 190 |
| Ia-4 | H | H | — | — | $CH_3$ | H | i-$C_3H_7$ | 170 |
| Ia-5 | $CF_3$ | H | — | — | H | H | $CH_3$ | 167 |
| Ia-6 | $CF_3$ | H | — | — | $CH_3$ | H | $C_2H_5$ | 180 |
| Ia-7 | $CF_3$ | H | — | — | $C_2H_5$ | H | $C_2H_5$ | 139 |
| Ia-8 | $CF_3$ | H | — | — | $CH_3$ | H | i-$C_3H_7$ | 173 |
| Ia-9 | $CF_3$ | H | — | — | $CH_3$ | H |  | 160 |
| Ia-10 | $CF_3$ | H | — | — | $CH_3$ | H | i-$C_4H_9$ | 173 |
| Ia-11 | $CF_3$ | H | — | — | $CH_3$ | H | 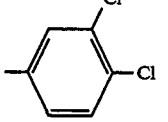 | 145 |
| Ia-12 | $CF_3$ | H | — | — | H | H | 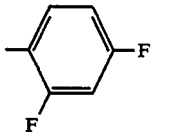 | 236 |
| Ia-13 | $CF_3$ | H | — | — | $CH_3$ | H | 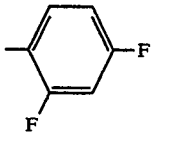 | 238–239 |
| Ia-14 | $CF_3$ | H | — | — | H | H | 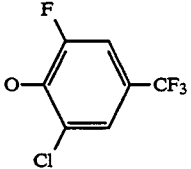 | 185–186 |
| Ia-15 | 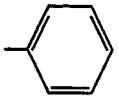 | H | — | — | H | H |  | 110 |

TABLE 3-continued (Ia)

| Ex. No. | X | Y | Z | n | M | L | A | Melting point/°C. |
|---|---|---|---|---|---|---|---|---|
| Ia-16 | CF$_3$ | H | — | — | CH$_3$ | H | 3-fluorophenyl | 143 |
| Ia-17 | Cl | Cl | — | — | CH$_3$ | H | CH$_3$ | 194 |
| Ia-18 | Cl | Cl | — | — | H | —CH$_2$—CH$_2$—CH$_2$—CH$_2$— | | >220 |
| Ia-19 | CF$_3$ | H | — | — | H | —CH$_2$—CH$_2$—CH$_2$—CH$_2$— | | 180 |
| Ia-20 | Cl | Cl | — | — | CH$_3$ | H | cyclopropyl | 165 |
| Ia-21 | Cl | Cl | — | — | C$_2$H$_5$ | H | CH$_3$ | 178 |
| Ia-22 | Cl | Cl | — | — | CH$_3$ | H | cyclopentyl | 188 |
| Ia-23 | Cl | Cl | — | — | CH$_3$ | H | i-C$_3$H$_7$ | >220 |
| Ia-24 | Cl | Cl | — | — | CH$_3$ | H | i-C$_4$H$_9$ | 150 |
| Ia-25 | Cl | Cl | — | — | CH$_3$ | H | C$_2$H$_5$ | 140 |
| Ia-26 | Br | H | — | — | CH$_3$ | H | CH$_3$ | 198 |
| Ia-27 | H | H | — | — | H | H | —CH$_2$-phenyl | 164 |
| Ia-28 | H | H | — | — | H | H | —CH(CH$_3$)-phenyl | 161 |
| Ia-29 | Cl | Cl | 4-CH$_3$-phenyl | — | — | H | CH$_3$ | 155–156 |
| Ia-30 | Cl | Cl | 4-Cl-phenyl | — | — | H | CH$_3$ | 145–150 |
| Ia-31 | Cl | Cl | 3-Cl-phenyl | — | — | H | CH$_3$ | 175–180 |
| Ia-32 | Cl | Cl | —CH$_2$-(4-Cl-phenyl) | — | — | H | CH$_3$ | 195–200 |
| Ia-33 | Cl | Cl | —CH$_2$-phenyl | — | — | H | CH$_3$ | 205–208 |

TABLE 3-continued (Ia)

| Ex. No. | X | Y | Z | n | M | L | A | Melting point/°C. |
|---|---|---|---|---|---|---|---|---|
| Ia-34 | Cl | Cl | — | — | —CH₂—(3-Cl-phenyl) | H | CH₃ | 225–230 |
| Ia-35 | Cl | Cl | — | — | —CH₂—(3-CF₃-phenyl) | H | CH₃ | 185–190 |
| Ia-36 | Cl | Cl | — | — | —CH₂—(4-CH₃-phenyl) | H | CH₃ | 210–215 |
| Ia-37 | Cl | Cl | — | — | 2-Cl-phenyl | H | CH₃ | 180–185 |
| Ia-38 | Cl | Cl | — | — | 4-OCH₃-phenyl | H | CH₃ | 183–184 |
| Ia-39 | Cl | Cl | — | — | H | H | 4-Cl-phenyl | 260–262 |
| Ia-40 | Cl | Cl | — | — | phenyl | H | CH₃ | 202–204 |
| Ia-41 | Cl | H | — | — | H | H | 3-CF₃-phenyl | Harz |
| Ia-42 | CF₃ | H | — | — | 4-OCH₃-phenyl | H | CH₃ | 135–7 |
| Ia-43 | CF₃ | H | — | — | 4-Cl-phenyl | H | CH₃ | 168 |

TABLE 3-continued (Ia)

| Ex. No. | X | Y | Z | n | M | L | A | Melting point/°C. |
|---|---|---|---|---|---|---|---|---|
| Ia-44 | $CF_3$ | H | — | — | —$CH_2$—(phenyl) | H | $CH_3$ | 142 |
| Ia-45 | $CF_3$ | H | — | — | —$CH_2$—(4-Cl-phenyl) | H | $CH_3$ | 160–2 |
| Ia-46 | $CF_3$ | H | — | — | —$CH_2$—(4-$CH_3$-phenyl) | H | $CH_3$ | 170 |
| Ia-47 | $CF_3$ | H | — | — | —$CH_2$—(2-Cl-phenyl) | H | $CH_3$ | 50–3 |
| Ia-48 | $CF_3$ | H | — | — | —$CH_2$—(3-Cl-phenyl) | H | $CH_3$ | 122 |
| Ia-49 | $CF_3$ | H | — | — | phenyl | H | $CH_3$ | 140–2 |
| Ia-50 | $CF_3$ | H | — | — | 2-Cl-phenyl | H | $CH_3$ | 130 |
| Ia-51 | $CF_3$ | H | — | — | 4-$CH_3$-phenyl | H | $CH_3$ | 152 |
| Ia-52 | $CF_3$ | H | — | — | 3-Cl-phenyl | H | $CH_3$ | 162–5 |
| Ia-53 | $CF_3$ | H | — | — | 3-$CF_3$-phenyl | H | $CH_3$ | 124–5 |

TABLE 3-continued (Ia)

| Ex. No. | X | Y | Z | n | M | L | A | Melting point/°C. |
|---|---|---|---|---|---|---|---|---|
| Ia-54 | CF₃ | H | — | — | H | H | 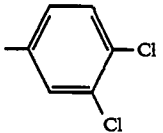 2,6-dichlorophenyl | 236 |
| Ia-55 | CF₃ | H | — | — | H | H | —CH₂—CH₂—phenyl | 114–116 |
| Ia-56 | CF₃ | H | — | — | H | H | —CH₂—phenyl | 139–141 |
| Ia-57 | CF₃ | H | — | — | CH₃ | H | —CH₂—CH₂—phenyl | 148–150 |
| Ia-58 | CF₃ | H | — | — | CH₃ | H | —CH₂—phenyl | 116–118 |
| Ia-59 | CF₃ | H | — | — | H | —(CH₂)₂—S—CH₂— | | 188–190 |
| Ia-60 | CF₃ | H | — | — | H | —(CH₂)₃— | | 184–186 |
| Ia-61 | CF₃ | H | — | — | H | H | —CH₂—C(CH₃)₃ | 178–180 |
| Ia-62 | CF₃ | H | — | — | CH₃ | H | —CH₂—C(CH₃)₃ | 173–175 |
| Ia-63 | CF₃ | H | — | — | H | H | —CH₂-cyclopentyl | 232–234 |

EXAMPLE 5

Synthesis of the intermediates (III)

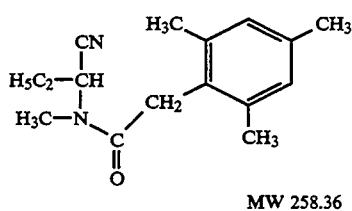

(III)

N-(α-cyanopropyl)-N-methyl-2,4,6-trimethyl-
phenylacetamide

MW 258.36

9.82 g (0.1 mol) of N-(α-cyanopropyl)-methylamine and 10.12 g of triethylamine are dissolved in 120 ml of tetrahydrofuran and the mixture is cooled to 0° C. 19.28 g (0.098 mol) of 2,4,6-trimethylphenylacetic acid chloride are then added dropwise in the course of one hour at 0° C. When the procedure has ended, the solution is introduced into a mixture of 500 ml of glacial acetic acid and 50 ml of 1-normal HCl solution, and the precipitate which is obtained in this process is filtered off and dried.

22.9 g (91% of theory) of N-(α-cyanopropyl)-N-methyl-2,4,6-trimethylphenylacetamide are obtained.

EXAMPLE 6

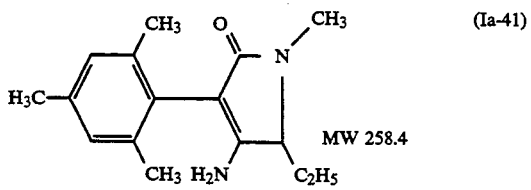

(Ia-41)

MW 258.4

4-amino-5-ethyl-1-methyl-3-(2,4,6-trimethylphenyl)-
pyrrolin-2-one

Process aβ

1.2 g (0.12 mol) of sodium hydride are dissolved in 60 ml of absolute toluene, and 22.5 g of N-(α-cyanopropyl)-N-methyl-2,4,6-trimethylphenylacetamide, dissolved in 100 ml of absolute toluene, are then added dropwise while cooling with an ice-bath. The mixture is then stirred until hydrogen is no longer evolved. The reaction solution is subsequently concentrated in vacuo, the residue is taken up in water, the mixture is acidified at 0°–20° C. using concentrated HCl solution, and the precipitate which is obtained in this process is filtered off. This precipitate is dried in vacuo at 70° C. using phosphorus pentoxide, if appropriate after previously having been extracted by boiling with a mixture of chloroform, methyl tertiary butyl ether and n-hexane.

17.4 g (77.4% of theory) of 4-amino-5-ethyl-1-methyl-3-(2,4,6-trimethylphenyl)-pyrrolin-2-one of melting point 192° C. are obtained.

EXAMPLE 7

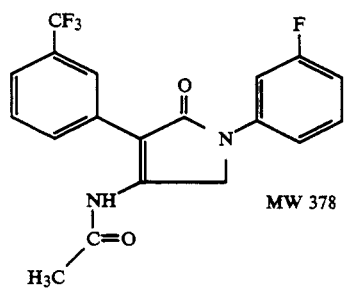

4-acetylamino-1-(3-fluorophenyl)-3-(3-trifluoromethylphenyl)-pyrrolin-2-one

Process bα

2.0 g (5.95 mMol) of 4-amino-1-(3-fluorophenyl)-3-(3-trifluoromethylphenyl)-pyrrolin-2-one (Ia-1) and 40 ml of acetic acid chloride are refluxed for 4 hours. The resulting suspension is introduced into 250 ml of ice-water while cooling with an ice-bath and extracted three times using 100 ml portions of methylene chloride, the collected organic phases are washed with saturated ammonium chloride solution and dried with magnesium sulphate, and the methylene chloride is finally removed in vacuo.

The resulting pale grey solid is stirred with methyl tertiary butyl ether, the suspension is filtered, and the solid is dried.

1.3 g (57.8% of theory) of 4-acetylamino-1-(3-fluorophenyl)-3-(3-trifluoromethylphenyl)-pyrrolin-2-one of a melting point of 115° C. are obtained.

Analogous reactions are carried out following this general procedure. The yields differ between 35 and 90%. In individual cases the product was chromatographed over silica gel (eluent toluene: acetone (3:1)).

The end products of the formula (Ib) in which B represents acetyl and which are listed below in Table 4 are obtained analogously to Example 7 and taking into consideration the information in the description of process (bα) according to the invention.

TABLE 4

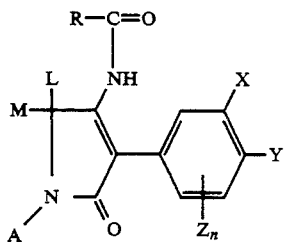

(Ib)

| Ex. No. | X | Y | Z | n | L | M | A | R | Melting point/°C. |
|---|---|---|---|---|---|---|---|---|---|
| Ib-2 | CF₃ | H | — | — | CH₃ | H | △ | CH₃ | 80 |
| Ib-3 | CF₃ | H | — | — | —CH₂—C₆H₅ | H | H | CH₃ | 182–183 |
| Ib-4 | 3-F, 4-O-(2-Cl-4-CF₃-phenyl) | H | — | — | H | H | C₆H₅ | CH₃ | 162–163 |
| Ib-5 | CF₃ | H | — | — | CH₃ | H | CH₃ | CH₃ | Resin |
| Ib-6 | CF₃ | H | — | — | H | H | △ | CH₃ | 145 |
| Ib-7 | CF₃ | H | — | — | CH₃ | H | C₂H₅ | CH₃ | 70 |

TABLE 4-continued (Ib) structure: R—C=O attached via NH to vinyl group with L, M substituents, connected to aryl ring with X, Y, Z_n substituents, and to N(A)—C=O ring.

| Ex. No. | X | Y | Z | n | M | L | A | R | Melting point/°C |
|---|---|---|---|---|---|---|---|---|---|
| Ib-8 | $CF_3$ | H | — | — | $CH_3$ | H | 2,4-difluorophenyl | $CH_3$ | 96 |
| Ib-9 | $CF_3$ | H | — | — | H | H | $i\text{-}C_3H_7$ | $CH_3$ | 143 |
| Ib-10 | Cl | Cl | — | — | $CH_3$ | H | $CH_3$ | $CH_3$ | 183 |
| Ib-11 | H | H | — | — | H | H | $-CH_2$-phenyl | $CH_3$ | 219 |
| Ib-12 | H | H | — | — | H | H | $-CH(CH_3)$-phenyl | $CH_3$ | 78 |
| Ib-13 | $CF_3$ | H | — | — | H | H | 2,4-difluorophenyl | $CH_3$ | 236–237 |
| Ib-14 | $CF_3$ | H | — | — | H | H | 3,4-dichlorophenyl | $CH_3$ | 202 |
| Ib-15 | Cl | H | — | — | H | H | 3,4-dichlorophenyl | $CH_3$ | 234 |
| Ib-16 | $CF_3$ | H | — | — | H | $-(CH_2)_4-$ | | $CH_3$ | 165 |
| Ib-17 | Cl | Cl | — | — | H | $CH_3$ | $i\text{-}C_4H_9$ | $CH_3$ | 88–98 |
| Ib-18 | Cl | Cl | — | — | H | $CH_3$ | $C_2H_5$ | $CH_3$ | 143–145 |
| Ib-19 | Cl | Cl | — | — | H | $CH_3$ | cyclopropyl | $CH_3$ | 184–187 |
| Ib-20 | Cl | Cl | — | — | H | $C_2H_5$ | $CH_3$ | $CH_3$ | 168–169 |
| Ib-21 | Cl | Cl | — | — | H | $CH_3$ | cyclopentyl | $CH_3$ | 190–193 |
| Ib-22 | Cl | Cl | — | — | $CH_3$ | H | $i\text{-}C_3H_7$ | $CH_3$ | Resin |
| Ib-23 | Cl | Cl | — | — | H | H | 4-chlorophenyl | $CH_3$ | 265 |

TABLE 4-continued

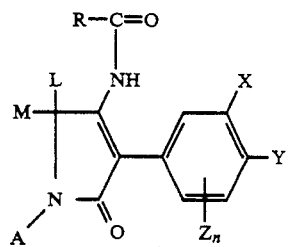
(Ib)

| Ex. No. | X | Y | Z | n | L | M | A | R | Melting point/°C. |
|---|---|---|---|---|---|---|---|---|---|
| Ib-24 | Cl | H | — | — | H | H | 3-CF$_3$-phenyl | CH$_3$ | 225–226 |
| Ib-25 | CF$_3$ | H | — | — | —CH$_2$-(3-CF$_3$-phenyl) | | H | CH$_3$ | CH$_3$ | 72 |
| Ib-26 | Cl | Cl | — | — | H | H | 4,5-dichloro-2-(NHC(O)CH$_3$)-phenyl | CH$_3$ | >250 |

| Ex. No. | X | Y | Z | n | L | M | A | R | Melting point/°C. |
|---|---|---|---|---|---|---|---|---|---|
| Ib-27 | CF$_3$ | H | — | — | H | H | cyclopropyl | C$_2$H$_5$ | 117 |
| Ib-28 | CF$_3$ | H | — | — | H | H | cyclopropyl | C(CH$_3$)$_3$ | 132 |
| Ib-29 | CF$_3$ | H | — | — | H | H | cyclopropyl | CH$_2$—C(CH$_3$)$_3$ | 153 |
| Ib-30 | CF$_3$ | H | — | — | —CH$_2$-(3-Cl-phenyl) | H | CH$_3$ | CH$_3$ | 54–57 |
| Ib-31 | CF$_3$ | H | — | — | —CH$_2$-phenyl | H | CH$_3$ | CH$_3$ | 115–117 |
| Ib-32 | CF$_3$ | H | — | — | —CH$_2$-(4-CH$_3$-phenyl) | H | CH$_3$ | CH$_3$ | 145–147 |
| Ib-33 | CF$_3$ | H | — | — | 4-CH$_3$-phenyl | H | CH$_3$ | CH$_3$ | 75–77 |

| Ex. No. | X | Y | Z | n | M | L | A | R | Melting point/°C. |
|---|---|---|---|---|---|---|---|---|---|

TABLE 4-continued (Ib)

Structure: R—C(=O)—NH— on vinyl carbon with L, M substituents; other vinyl carbon bears aryl group (with X, Y, Z_n) and C(=O)—N(A)— ring closure.

| No. | R | L | M | — | (substituent) | X | Y | Z | m.p. (°C) |
|---|---|---|---|---|---|---|---|---|---|
| Ib-34 | CF$_3$ | H | — | — | —CH$_2$—C$_6$H$_4$—Cl (p) | H | CH$_3$ | CH$_3$ | 155–157 |
| Ib-35 | CF$_3$ | H | — | — | —CH$_2$—CH$_2$—C$_6$H$_5$ | H | H | CH$_3$ | 63–66 |
| Ib-36 | CF$_3$ | H | — | — | —CH$_2$—C$_6$H$_5$ | H | H | CH$_3$ | 112–114 |
| Ib-37 | CF$_3$ | H | — | — | CH$_3$—CH$_2$—C$_6$H$_5$ | CH$_3$ | H | CH$_3$ | 73–76 |
| Ib-38 | CF$_3$ | H | — | — | —CH$_2$—C$_6$H$_5$ | CH$_3$ | H | CH$_3$ | 77–80 |
| Ib-39 | CF$_3$ | H | — | — | —C$_6$H$_4$—OCH$_3$ (p) | H | CH$_3$ | CH$_3$ | 134–137 |
| Ib-40 | CF$_3$ | H | — | — | H | —CH$_2$—CH$_2$—S—CH$_2$— | | CH$_3$ | 199–201 |
| Ib-41 | CF$_3$ | H | — | — | H | —CH$_2$—CH$_2$—CH$_2$— | | CH$_3$ | 128–130 |
| Ib-42 | CF$_3$ | H | — | — | H | H | CH$_2$—C(CH$_3$)$_3$ | CH$_3$ | 113–115 |
| Ib-43 | CF$_3$ | H | — | — | CH$_3$ | H | CH$_2$—C(CH$_3$)$_3$ | CH$_3$ | 159–160 |
| Ib-44 | CF$_3$ | H | — | — | —C$_6$H$_4$—Cl (p) | H | CH$_3$ | CH$_3$ | 93–95 |

USE EXAMPLES

In the use examples which follow, the compound listed below was employed as comparison substance:

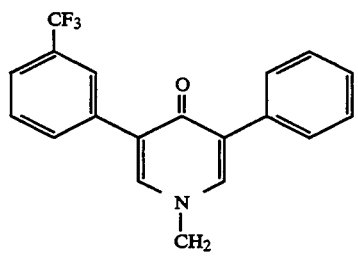

(A)

1-Methyl-3-phenyl-5-(2,α,α-trifluoro-m-tolyl)-4-pyridone [fluridone], known from R. Wegler, Chemie der Pflanzenschutz und Schädlingsbekäimpfungsmittel [Chemistry of Crop Protection and Pesticides] 5, Herbizide, Axel-Springer-Verlang, Berlin, Heidelberg, New York 1977, page 309.

EXAMPLE A

Post-emergence Test

| | | |
|---|---|---|
| Solvent: | 5 parts by weight of acetone | |
| Emulsifier: | 1 part by weight of alkylaryl polyglycol ether | |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control. The figures denote:

0% = no action (like untreated control)
100% = total destruction

A clearly superior activity and crop plant selectivity compared with the prior art is shown, in this test, for example by the compounds of the following Preparation Examples Ia-2, Ia-3, Ia-11, Ib-6 and Ib-9.

EXAMPLE B
Pro-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

A clearly superior activity and crop plant selectivity compared with the prior art is shown, in this test, for example by the compounds of the following Preparation Example: Ib-9.

It will be understood that the specification and examples are illustrative but not limitative of the present invention and that other embodiments within the spirit and scope of the invention will suggest themselves to those skilled in the art.

What is claimed is:

1. A 4-(substituted)amino-3-arylpyrrolinone derivative of the general formula (I) wherein

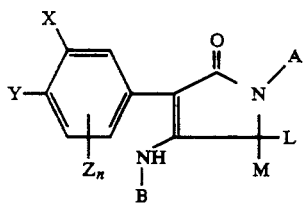

(I)

X represents hydrogen, fluorine, chlorine, bromine, methyl, ethyl, methoxy, ethoxy, n- or i-propoxy, trifluoromethyl, trifluoromethoxy, or
Y represents hydrogen, fluorine, chlorine, bromine, methyl, methoxy, trifluoromethoxy or trifluoromethyl,
n represents 0 and A represents methyl, ethyl, n-propyl, iso-propyl, n-, iso-, sec.- or tert.-butyl, or represents an in each case straight-chain or branched radical from the series comprising pentyl, hexyl, heptyl, octyl, halogeno-$C_1$–$C_3$-alkyl, allyl, propargyl, methoxymethyl, methoxyethyl, ethoxymethyl, ethoxyethyl, cyclopropyl, cyclopentyl, cyclohexyl, or represents phenyl or benxyl, each of which is unsubsttituted or monosubstituted to trisubstituted by identical or different substituents from the series comprising fluorine, chlorine, trifluoromethyl,
B represents hydrogen, the group —CO—R or the group

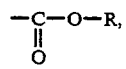

L represents hydrogen or an optionally halogen-substituted straight-chain or branched radical from the series comprising $C_1$–$C_8$-alkyl, cycloalkyl which has 3 to 6 ring atoms or aryl which is optionally substituted by fluorine, chlorine, bromine, methyl, ethyl, propyl, iso-propyl, methoxy, ethoxy, trifluoromethyl or nitro,
M represents hydrogen or a straight-chain or branched radical from the series comprising $C_1$–$C_6$-alkyl,
or in which
A and L or L and M together with the atoms to which they are bonded form a 3 to 6-membered ring, optionally substituted by $C_1$–$C_4$-alkyl, and/or interrupted by oxygen/sulphur,
R represents an optionally halogen-substituted straight-chain or branched radical from the series comprising $C_1$–$C_8$-alkyl, $C_1$–$C_4$-alkenyl, $C_1$–$C_6$-alkoxy-$C_2$–$C_4$-alkyl, cycloalkyl which has 3 to 6 ring atoms and the enantiomeric compounds of the formula (I) with the exception of the compounds: 4-amino-1-cyclopropyl-3-(3-trifluoromethylphenyl)-3-pyrrolin-2-one and 4-amino-1-isopropyl-3-(3-trifluoromethylphenyl)-3-pyrrolin-2-one.

2. A compound according to claim 1, wherein such compound is 4-amino-1-cyclopropyl-5-methyl-3-phenyl-pyrrolin-2-one of the formula

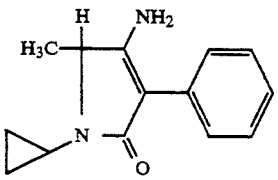

3. A compound according to claim 1 wherein such compound is 4-amino-1-isopropyl-3-phenyl-pyrrolin-2-one of the formula

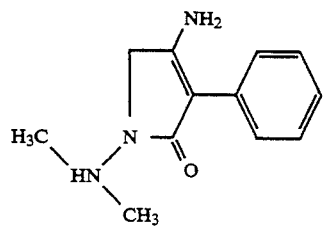

4. A compound according to claim 1, wherein such compound is 4-acetylamino-1-cyclopropyl-3-(3-trifluoromethyl-phenyl)-pyrrolin-2-one of the formula

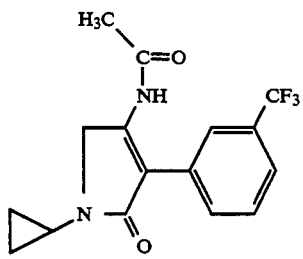

5. A compound according to claim 1, wherein such compound is 4-acetylamino-1-isopropyl-3-(3-trifluoromethyl-phenyl)-pyrrolin-2-one of the formula

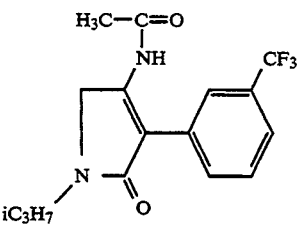

6. A herbicidal composition comprising a herbicidally effective amount of a compound according to claim 1 and a diluent.

7. A method of combating unwanted vegetation which comprises applying to such vegetation or to a locus from which it is desired to exclude such vegetation a herbicidally effective amount of a compound according to claim 1.

8. A method according to claim 7, wherein such compound is 4-amino-1-cyclopropyl-5-methyl-3-phenyl-pyrrolin-2-one 4-amino-1-isopropyl-3-phenyl-pyrrolin-2-one 4-acetylamino-1-cyclopropyl-3-(3-trifluoromethyl-phenyl)-pyrrolin-2-one 4-acetylamino-1-isopropyl-3-(3-trifluoromethyl-phenyl)-pyrrolin-2-one.

* * * * *

UNITED STATES PATENT AND TRADEMARK OFFICE
CERTIFICATE OF CORRECTION

PATENT NO. : 5,338,860
DATED : August 16, 1994
INVENTOR(S) : Bernd Baasner, et al.

It is certified that error appears in the above-indentified patent and that said Letters Patent is hereby corrected as shown below:

Column 62, line 28,    delete "$C_1$-$C_6$-alkyl" and substitute --$C_1$-$C_8$-alkyl--

Signed and Sealed this

Twenty-first Day of April, 1998

Attest:

BRUCE LEHMAN

*Attesting Officer*    *Commissioner of Patents and Trademarks*